United States Patent
Merino et al.

(10) Patent No.: US 9,284,588 B2
(45) Date of Patent: Mar. 15, 2016

(54) PROMOTERS FOR EXPRESSING GENES IN A FUNGAL CELL

(75) Inventors: Sandra Merino, West Sacramento, CA (US); Debbie Yaver, Davis, CA (US)

(73) Assignee: NOVOZYMES, INC., Davis, CA (US)

( * ) Notice: Subject to any disclaimer, the term of this patent is extended or adjusted under 35 U.S.C. 154(b) by 0 days.

(21) Appl. No.: 13/885,145

(22) PCT Filed: Dec. 15, 2011

(86) PCT No.: PCT/US2011/065287
§ 371 (c)(1),
(2), (4) Date: Jul. 15, 2013

(87) PCT Pub. No.: WO2012/083081
PCT Pub. Date: Jun. 21, 2012

(65) Prior Publication Data
US 2013/0288298 A1    Oct. 31, 2013

Related U.S. Application Data

(60) Provisional application No. 61/423,909, filed on Dec. 16, 2010.

(51) Int. Cl.
*C12P 21/00*    (2006.01)
*C12N 9/08*    (2006.01)
*C12N 15/80*    (2006.01)

(52) U.S. Cl.
CPC ............... *C12P 21/00* (2013.01); *C12N 9/0065* (2013.01); *C12N 15/80* (2013.01)

(58) Field of Classification Search
None
See application file for complete search history.

(56) References Cited

U.S. PATENT DOCUMENTS

2009/0298126 A1* 12/2009 Merino .................. 435/69.7

OTHER PUBLICATIONS

Sequence CB897728, retrieved Jul. 24, 2014 from: http://www.ebi.ac.uk/Tools/dbfetch/dbfetch?db=embl&id=cb897728&format=default&style=default&Retrieve=Retrieve.*
Sequence CB897728, retrieved Jul. 24, 2014 from: http://www.ebi.ac.uk/Too~s/dbfetch/dbfetch?db=emb~&id=cb897728&f~rmat=default&style=default&Retrieve=Retrieve.*
Bergquist et al, 2004, Biochem Soc Trans 32(2), 293-297.
Diener et al, 2004—EBI Access No. CF 867685.
Diener et al, 2004, FEMS Microbiol Lett 230(2), 275-282.
Foreman et al, 2003—EBI Acces No. CB897728.
Foreman et al, 2003, J Biol Chem 278(34), 31988-31997.
Uusitala et al, 1991, J Biotechnol 17(1), 35-49.

* cited by examiner

*Primary Examiner* — Michele K Joike
*Assistant Examiner* — Mindy G. Brown
(74) *Attorney, Agent, or Firm* — Robert L. Starnes (57) ABSTRACT

The present invention relates to isolated promoters and constructs, vectors, and fungal host cells comprising such promoters operably linked to polynucleotides encoding polypeptides. The present invention also relates to methods for producing such polypeptides.

11 Claims, 3 Drawing Sheets

```
1    TTGTGCACGGCTTTGGGTTAGCAAATGCGGAGAAAGAAAGCAAGGCCGAAGTGCCAGAAT
61   AGAAGCAGAGGCCACAGTACGCATTCCTTCTTCTTCCCCAACTAACACGGATGGGGAGTA
121  GGTAGACGCGTGCCATCGAGATGATGACGGTACTTGGACGACGGCTCGAGGATCGCCATA
181  CTGCCAAAGTACCGAGAGCTCACCACCAAGGGATACGCCCCTCAGCAACGTGCGAGCCCC
241  CGGATAGTTGCATCCGAAGAGAAGCGGCAAGGCATTGATTACTCCAAGTCTCCTGATTTC
301  CCAGCAGCCAGCTCGCCCCCCTTGCCCCGATTCGAACAGCTTCCACCCTCCACCAAGCTA
361  AACGACCCCGCCTGTTGCTCGAGGAGCCGCGGGTCTTTGAAATTGCGAGGCTTCGGTTCG
421  TCAGCACCGACAGCGATGACACAACCGCCGCCAATGGCGTTGCACCCGCAGATCCAGATG
481  AGGCCTGCGAGCGGCGTGATCGCGACATTGGCTGGCAGGCCGGTGACATGCTGGAGAAAC
541  GCGGGGTTCGTGCCTCCAGCCAAGTCCAGACCCCTCCTCCTCCTCGTCTGGTTGCTCTCC
601  TCCTCTTGGTCGGGTGGTTTGTACTGTGCATTTATATTGTTTGTTGTCTCCTCTTTTCCG
661  TCCTTTGGTCCTTCTCTTCTTCCTCCTCCTCTGTGTCCTTCTTTCCCTCGAGCTCAT
721  CTGTTAGCGGATTCTCGACAAGAGTCGGCCAACATTGGGCTTGCACTTACACCAACCAAC
781  ACCACCTACTAGATACCCCCCAACTGCAACCCTCTATTTCGTCTTCAGAATCAATCAAA
841  ACACATCCAAGAAACCAACGAGAACAGCAAAA
```

PROMOTERS FOR EXPRESSING GENES IN A FUNGAL CELL

CROSS-REFERENCE TO RELATED APPLICATION

This application is a National Phase filing under 35 U.S.C. §371 of International Application No. PCT/US2011/065287, filed Dec. 15, 2011, which claims priority to U.S. Provisional Application Ser. No. 61/423,909, filed Dec. 16, 2010. The contents of these applications are hereby incorporated by reference in their entireties.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods for producing polypeptides. The present invention also relates to isolated promoters and to nucleic acid constructs, vectors, and host cells comprising the promoters operably linked to polynucleotides encoding the polypeptides.

2. Description of the Related Art

The recombinant production of a polypeptide in a fungal host cell, e.g., a filamentous fungal cell, may provide for a more desirable vehicle for producing the polypeptide in commercially relevant quantities.

Recombinant production of a polypeptide is accomplished by constructing an expression cassette in which the DNA coding for the polypeptide is placed under the expression control of a promoter, excised from a gene, suitable for the host cell. The expression cassette is introduced into the host cell, usually by plasmid-mediated transformation. Production of the polypeptide is then achieved by culturing the transformed host cell under inducing conditions necessary for the proper functioning of the promoter contained on the expression cassette.

The use of a fungal host cell for the recombinant production of polypeptides generally requires the availability of promoters that are suitable for controlling the expression of the polypeptides in the host cell. Consequently, there is a need in the art for new promoters for controlling the recombinant expression of genes.

The present invention provides improved methods for producing a polypeptide in a fungal host cell.

SUMMARY OF THE INVENTION

The present invention relates to methods for producing a polypeptide, comprising: (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence having at least 60% sequence identity to SEQ ID NO: 1; (ii) a promoter comprising a nucleotide sequence that hybridizes under at least medium stringency conditions with SEQ ID NO: 1 or the full-length complement thereof; (iii) a promoter comprising SEQ ID NO: 1; (iv) a promoter comprising a subsequence of (i), (ii), or (iii) that retains promoter activity; and (v) a mutant, hybrid, or tandem promoter of (i), (ii), (iii), or (iv); wherein the polynucleotide encoding the polypeptide is foreign to the promoter; and (b) isolating the polypeptide from the cultivation medium.

The present invention also relates to isolated promoters selected from the group consisting of (i) a promoter comprising a nucleotide sequence having at least 60% sequence identity to SEQ ID NO: 1; (ii) a promoter comprising a nucleotide sequence that hybridizes under at least medium stringency conditions with SEQ ID NO: 1 or the full-length complement thereof; (iii) a promoter comprising SEQ ID NO: 1; (iv) a promoter comprising a subsequence of (i), (ii), or (iii) that retains promoter activity; and (v) a mutant, hybrid, or tandem promoter of (i), (ii), (iii), or (iv).

The present invention also relates to constructs, vectors, and fungal host cells comprising a promoter of the present invention operably linked to a polynucleotide encoding a polypeptide.

DEFINITIONS

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding the polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like, with a nucleic acid construct or expression vector comprising a polynucleotide of interest. The term "host cell" encompasses any progeny of a parent cell that is not identical to the parent cell due to mutations that occur during replication.

Hybrid promoter: The term "hybrid promoter" means portions of two or more (e.g., several) promoters that are linked together to generate a sequence that is a fusion of the portions of the two or more promoters, which when operably linked to a coding sequence mediates the transcription of the coding sequence into mRNA.

Isolated: The term "isolated" means a substance in a form or environment that does not occur in nature. Non-limiting examples of isolated substances include (1) any non-naturally occurring substance, (2) any substance including, but not limited to, any enzyme, variant, polynucleotide, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). A polypeptide of interest may be used in industrial applications in the form of a fermentation broth product, that is, the polypeptide is a component of a fermentation broth used as a product in industrial applications (e.g., ethanol production). The fermentation broth product will in addition to the polypeptide of interest comprise additional ingredients used in the fermentation process, such as, for example, cells (including, the host cells containing the gene encoding the polypeptide of interest which are used to produce the polypeptide), cell debris, biomass, fermentation media and/or fermentation products. The fermentation broth may be optionally subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having biological activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic.

Operably linked: The term "operably linked" means a configuration in which a control sequence is placed at an appropriate position relative to the coding sequence of a polynucleotide such that the control sequence directs expression of the coding sequence.

Polypeptide fragment: The term "polypeptide fragment" means a polypeptide having one or more (e.g., several) amino acids absent from the amino and/or carboxyl terminus of a mature polypeptide; wherein the fragment has biological activity. In one aspect, the fragment has at least 85%, e.g., at least 90% or at least 95% of the number of amino acids as the mature polypeptide.

Polypeptide variant: The term "polypeptide variant" means a polypeptide having biological activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Promoter: The term "promoter" means a DNA sequence that binds RNA polymerase and directs the polymerase to the correct downstream transcriptional start site of a polynucleotide encoding a polypeptide to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

Promoter variant: The term "promoter variant" means a promoter comprising an alteration, i.e., a substitution, insertion, and/or deletion, at one or more (e.g., several) positions. A substitution means replacement of the nucleotide occupying a position with a different nucleotide; a deletion means removal of the nucleotide occupying a position; and an insertion means adding a nucleotide adjacent to and immediately following the nucleotide occupying a position. The term "promoter variant" will also encompass natural variants and in vitro generated variants obtained using methods well known in the art such as classical mutagenesis, site-directed mutagenesis, and DNA shuffling.

Sequence identity: The relatedness between two amino acid sequences or between two polynucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0, or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0, or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence wherein the subsequence encodes a fragment having biological activity, or absent from the 5' and/or 3' end of a promoter sequence wherein the promoter subsequence has promoter activity. In one aspect, the subsequence has at least 85%, e.g., at least 90% or at least 95% of the number of nucleotides as the mature polypeptide coding sequence. In another aspect, the promoter subsequence has at least 85%, e.g., at least 90% or at least 95% of the number of nucleotides as the promoter sequence.

Tandem promoter: The term "tandem promoter" means two or more (e.g., several) promoters linked in tandem, each of which is operably linked to a coding sequence and mediates the transcription of the coding sequence into mRNA.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

The present invention relates to methods for producing a polypeptide, comprising: (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence having at least 60% sequence identity to SEQ ID NO: 1; (ii) a promoter comprising a nucleotide sequence that hybridizes under at least medium stringency conditions with SEQ ID NO: 1 or the full-length complement thereof; (iii) a promoter comprising SEQ ID NO: 1; (iv) a promoter comprising a subsequence of (i), (ii), or (iii) that retains promoter activity; and (v) a mutant, hybrid, or tandem promoter of (i), (ii), or (iv); wherein the polynucleotide encoding the polypeptide is foreign to the promoter; and (b) isolating the polypeptide from the cultivation medium.

In the production methods of the present invention, the cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of an enzyme. Procedures for determining enzyme activity are known in the art for many enzymes (see, for example, D. Schomburg and M. Salzmann (eds.), *Enzyme Handbook*, Springer-Verlag, New York, 1990).

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Promoters

The present invention also relates to isolated promoters selected from the group consisting of (i) a promoter comprising a nucleotide sequence having at least 60% sequence identity to SEQ ID NO: 1; (ii) a promoter comprising a nucleotide sequence that hybridizes under at least medium stringency conditions with SEQ ID NO: 1 or the full-length complement thereof; (iii) a promoter comprising SEQ ID NO: 1; (iv) a promoter comprising a subsequence of (i), (ii), or (iii) that retains promoter activity; and (v) a mutant, hybrid, or tandem promoter of (i), (ii), (iii), or (iv); and to constructs, vectors, and fungal host cells comprising the promoter operably linked to a polynucleotide encoding a polypeptide.

In one aspect, the isolated promoters have a sequence identity to SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have promoter activity.

In one embodiment, a promoter of the present invention comprises or consists of the nucleotide sequence of SEQ ID NO: 1 or an allelic variant thereof; or is a subsequence thereof having promoter activity. In another aspect, the promoter comprises or consists of the nucleotide sequence of SEQ ID NO: 1.

A subsequence of SEQ ID NO: 1 (i.e., a truncated promoter) comprises a truncation at the 5' end so that the sequence at the 3' end closest to the ATG codon is maintained. The subsequence can be at least 600 nucleotides, e.g., at least 700 nucleotides, at least 750 nucleotides, at least 800 nucleotides, at least 850 nucleotides, or at least 900 nucleotides, that has promoter activity.

In one aspect, the isolated promoters comprise nucleotide sequences that hybridize under very low stringency conditions, low stringency conditions, medium stringency conditions, medium-high stringency conditions, high stringency conditions, or very high stringency conditions with SEQ ID NO: 1 or a subsequence thereof; or the full-length complement of the foregoing (J. Sambrook, E. F. Fritsch, and T. Maniatis, 1989, *Molecular Cloning, A Laboratory Manual*, 2d edition, Cold Spring Harbor, N.Y.).

The polynucleotide SEQ ID NO: 1, or a subsequence thereof, may be used to design nucleic acid probes to identify and clone promoter DNA from strains of different genera or species according to methods well known in the art. In particular, such probes can be used for hybridization with the genomic DNA or cDNA of the genus or species of interest, following standard Southern blotting procedures, in order to identify and isolate the corresponding promoter DNA therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding promoter DNA (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described herein and has promoter activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the polynucleotide hybridizes to a labeled nucleic acid probe corresponding to SEQ ID NO: 1 or the full-length complement thereof, or a subsequence thereof, under very low to very high stringency conditions. Molecules to which the nucleic acid probe hybridizes under these conditions can be detected using, for example, X-ray film.

In one embodiment, the nucleic acid probe is SEQ ID NO: 1 or a subsequence thereof. In another embodiment, the nucleic acid probe is SEQ ID NO: 1.

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In another aspect, the isolated promoters may be mutants of a promoter comprising the polynucleotide sequence of SEQ ID NO: 1, or a subsequence thereof, that has promoter activity. The mutant promoters comprise one or more mutations (e.g., several) of SEQ ID NO: 1, or a subsequence thereof, that has promoter activity. Each mutation is an independent substitution, deletion, and/or insertion of a nucleotide. The introduction of a substitution, deletion, and/or insertion of a nucleotide into the promoter may be accomplished using any of the methods known in the art such as classical mutagenesis, site-directed mutagenesis, or DNA shuffling. Particularly useful is a procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpn I which is specific for methylated and hemimethylated DNA to digest the parental DNA template and to select for mutation-containing synthesized DNA. Other procedures known in the art may also be used.

In another aspect, the isolated promoters may be hybrid promoters comprising a portion of a promoter of the present invention and a portion of another promoter, e.g., a leader sequence of one promoter and the transcription start site from the other promoter; or a portion of one or more (e.g., several) promoters of the present invention and a portion of one or more (e.g., several) other promoters. The other promoter may be any promoter sequence which shows transcriptional activity in the fungal host cell of choice including a mutant, truncated, and hybrid promoter, and may be obtained from genes encoding extracellular or intracellular polypeptides either homologous or heterologous to the host cell. The other promoter sequence may also be a portion of a promoter of the present invention. The other promoter sequence may also be native or foreign to the polynucleotide encoding the polypeptide and native or foreign to the cell.

In another aspect, the isolated promoters may be tandem promoters comprising one or more (e.g., several) promoters of the present invention and one or more (e.g., several) other promoters. The one or more (e.g., several) other promoters may be promoters of the present invention. The one or more (e.g., several) other promoters may be promoters such as those exemplified below. Two or more (e.g., several) promoter sequences of the tandem promoter may simultaneously promote the transcription of the polynucleotide. Alternatively, one or more (e.g., several) of the promoter sequences of the tandem promoter may promote the transcription of the polynucleotide at different stages of growth of the cell. In one embodiment, the tandem promoter comprises two promoters. In another embodiment, the tandem promoter comprises three promoters. In another embodiment, the tandem promoter comprises four promoters. In another embodiment, the tandem promoter comprises five promoters.

Examples of other promoters useful in the construction of tandem promoters or hybrid promoters with the promoters of the present invention include the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, NA2-tpi promoter (a modified promoter from an *Aspergillus* neutral alpha-amylase gene in which the untranslated leader has been replaced by an untranslated leader from an *Aspergillus* those phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase; and mutant, truncated, and hybrid promoters thereof. Other promoters are described in U.S. Pat. No. 6,011,147 and by Romanos et al., 1992, *Yeast* 8: 423-488.

In the methods of the present invention, a hybrid or tandem promoter of the present invention will be understood to be foreign to a polynucleotide encoding a polypeptide even if the wild-type promoter is native to the polynucleotide. For example, in a tandem promoter consisting of at least two promoters, one of the promoters may be the wild-type promoter of the polynucleotide encoding the polypeptide.

Polypeptides

The term "polypeptide" is defined herein as a polypeptide encoded by a coding sequence that is foreign to a promoter of the present invention.

The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses polypeptides, which comprise a combination of partial and/or complete polypeptide sequences obtained from at least two different polypeptides wherein one or more (e.g., several) may be heterologous to the fungal cell. Polypeptides further include naturally occurring allelic and engineered variations of a polypeptide.

In one aspect, the polypeptide is an antibody, antigen, antimicrobial peptide, enzyme, growth factor, hormone, immunodilator, neurotransmitter, receptor, reporter protein, structural protein, and transcription factor.

In one embodiment, the enzyme is an oxidoreductase, transferase, hydrolase, lyase, isomerase, or ligase, in another embodiment, the enzyme is an acetylmannan esterase, acetylxylan esterase, alpha-galactosidase, alpha-glucosidase, alpha-glucuronidase, aminopeptidase, amylase, amyloglucosidase, arabinanase, arabinafuranosidase, beta-galactosidase, beta-glucosidase, beta-xylosidase, carbohydrase, carboxypeptidase, catalase, cellobiohydrolase, cellulase, chitinase, coumaric acid esterase, cutinase, cyclodextrin glycosyltransferase, deoxyribonuclease, endoglucanase, esterase, feruloyl esterase, GH61 polypeptide having cellutolytic enhancing activity, glucocerebrosidase, glucuronidase, hemicellulase, invertase, laccase, lipase, mannanase, mannosidase, mutanase, oxidase, pectinolytic enzyme, peroxidase, phospholipase, phytase, polyphenoloxidase, protease, ribonuclease, transglutaminase, urokinase, or xylanase.

In another aspect, the polypeptide is an albumin, collagen, tropoelastin, elastin, or gelatin.

In another aspect, the polypeptide is an expansin or a swollenin.

In another aspect, the polypeptide is hybrid polypeptide in which a region of one polypeptide is fused at the N-terminus or the C-terminus of a region of another polypeptide.

In another aspect, the polypeptide is a chimeric polypeptide in which one or more (e.g., several) regions of one polypeptide are replaced with one or more (e.g., several) regions from one or more (e.g., several) other polypeptides.

In another aspect, the polypeptide is a fusion polypeptide or cleavable fusion polypeptide in which one polypeptide is fused at the N-terminus or the C-terminus of another polypeptide. A fusion polypeptide is produced by fusing a polynucleotide encoding the one polypeptide to a polynucleotide encoding the other polypeptide. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin at al., 2003, *J. Ind. Microbiol. Biotechnol.* 3: 568-576; Svetina at al., 2000, *J. Biotechnol,* 76:

245-251; Rasmussen-Wilson et al., 1997, *Appl. Environ. Microbiol.* 63: 3488-3493; Ward et al., 1995, *Biotechnology* 13: 498-503; and Contreras at al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The polynucleotide encoding a polypeptide may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a polynucleotide encoding a polypeptide are known in the art and include isolation from genomic DNA, preparation from cDNA, or a combination thereof. The cloning of the polynucleotide from such genomic DNA can be effected, e.g., by using the polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the polynucleotide encoding the polypeptide, insertion of the fragment into a vector molecule, and incorporation of the recombinant vector into the fungal cell where multiple copies or clones of the polynucleotide will be replicated. The polynucleotide may be of genomic, cDNA, RNA, semisynthetic, synthetic origin, or any combinations thereof.

Nucleic Acid Constructs

The present invention also relates to nucleic acid constructs comprising a polynucleotide encoding a polypeptide operably linked to a promoter of the present invention and one or more (e.g., several) control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

A polynucleotide may be manipulated in a variety of ways to provide for expression of the polypeptide. Manipulation of the polynucleotide prior to its insertion into a vector may be desirable or necessary depending on the expression vector. The techniques for modifying a polynucleotide utilizing recombinant DNA methods are well known in the art.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus nicer* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-actor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

The present invention also relates to nucleic acid constructs for altering the expression of a gene encoding a polypeptide which is endogenous to a host cell. The constructs may contain the minimal number of components necessary for altering expression of the endogenous gene. In one embodiment, the nucleic acid constructs preferably comprise (a) a targeting sequence, (b) a promoter of the present invention, (c) an axon, and (d) a splice-donor site. Upon introduction of the nucleic acid construct into a cell, the construct inserts by homologous recombination into the cellular genome at the endogenous gene site. The targeting sequence directs the integration of elements (a)-(d) into the endogenous gene such that elements (b)-(d) are operably linked to the endogenous gene. In another embodiment, the nucleic acid constructs comprise (a) a targeting sequence, (b) a promoter of the present invention, (c) an exon, (d) a splice-donor site, (e) an intron, and (f) a splice-acceptor site, wherein the targeting sequence directs the integration of elements (a)-(f) such that elements (b)-(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more (e.g., several) targeting sequences can be used. For example, a circular plasmid or DNA fragment preferably employs a single targeting sequence, while a linear plasmid or DNA fragment preferably employs two targeting sequences.

The constructs further contain one or more (e.g., several) axons of the endogenous gene. An exon is defined as a DNA sequence which is copied into RNA and is present in a mature mRNA molecule such that the axon sequence is in-frame with the coding region of the endogenous gene. The exons can, optionally, contain DNA which encodes one or more (e.g., several) amino acids and/or partially encodes an amino acid. Alternatively, the exon contains DNA which corresponds to a 5' non-encoding region. Where the exogenous axon or exons encode one or more (e.g., several) amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another axon. Typically, the first axon lies 5' of the second axon, and the splice-donor site overlapping and flanking the first exon on its 3' side recognizes a splice-acceptor site flanking the second exon on the 5' side of the second axon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

The present invention further relates to methods for producing a polypeptide comprising (a) cultivating a homologously recombinant cell, having incorporated therein a transcription unit comprising a promoter of the present invention, an exon, and/or a splice donor site operably linked to a second axon of an endogenous polynucleotide encoding the polypeptide, under conditions conducive for production of the polypeptide, wherein the polynucleotide encoding the polypeptide is foreign to the promoter; and (b) recovering the polypeptide. The methods are based on the use of gene activation technology, for example, as described in U.S. Pat. No. 5,641,670.

Expression Vectors

The present invention also relates to recombinant expression vectors comprising a promoter of the present invention, a polynucleotide encoding a polypeptide, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide operably linked to a promoter of the present invention or a nucleic acid construct thereof into an appropriate vector for expression. In creating the expression vector, the coding sequence is located in the vector so that the coding sequence is operably linked to a promoter of the present invention.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy auxotrophs, and the like.

Examples of selectable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopius* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotides sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9103-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a promoter of the present invention operably linked to a polynucleotide encoding a polypeptide, which are advantageously used in the recombinant production of the polypeptide. A vector comprising a promoter of the present invention operably linked to a polynucleotide encoding a polypeptide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii,*

Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypociadium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminurn, Fusarium heterosporurn, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusariurn venenatum, Humicola insolens, Humicola lanuginosa, Mucor miehei, Myceliophthora thermophila, Neurospora crassa, Penicillin purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachialum, Trichoderma reesei, or Trichoderma viride cell.

In one aspect, the host cell is a Trichoderma host cell (e.g., a Trichoderma reesei host cell).

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Solo USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

The present invention is further described by the following examples which should not be construed as limiting the scope of the invention.

EXAMPLES

Strains

Trichoderma reesei RutC30 (ATCC 56765; Montenecourt and Eveleigh, 1979, Adv. Chem. Ser. 181: 289-301) was derived from Trichoderma reesei Qm6A (ATCC 13631; Mandels and Reese, 1957, J. Bacteriol. 73: 269-278).

Trichoderma reesei RutC30-2 is a mutagenized strain of Trichoderma reesei RutC30 (ATCC 56765; Montenecourt and Eveleigh, 1979, supra).

Media and Solutions

YP medium was composed of 10 g of yeast extract, 20 g of bacto tryptone, and deionized water to 1 liter.

Cellulase-inducing medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of trace metals solution, and deionized water to 1 liter.

Trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

STC buffer was composed of 1 M sorbitol, 10 mM $CaCl_2$, and 10 mM Tris-HCl, pH 7.5.

COVE plates were composed of 342 g of sucrose, 10 ml of COVE salts solution, 10 ml of 1 M acetamide, 10 ml of 1.5 M CsCl, 25 g of Noble agar, and deionized water to 1 liter.

COVE salts solution was composed of 26 g of KCl, 26 g of $MgSO_4$, 76 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na^2MoO_2.H_2O$, 10 g of $ZnSO_4.7H_2O$, and deionized water to 1 liter.

COVE2 plates were composed of 30 g of sucrose, 20 ml of COVE salts solution, 25 g of Noble agar, 10 ml of 1 M acetamide, and deionized water to 1 liter.

PDA plates were composed of 39 grams of potato dextrose agar and deionized water to 1 liter.

2XYT-Amp plates were composed of 10 g of tryptone, 5 g of yeast extract, 5 g of sodium chloride, 15 g of bacto agar, 100 mg and ampicillin, and deionized water to 1 liter.

LB medium was composed of 10 g of tryptone, 5 g of yeast extract, 5 g of sodium chloride, and deionized water to 1 liter.

SOC medium was composed of 2% tryptone, 0.5% yeast extract, 10 mM NaCl, 2.5 mM KCl, 10 mM $MgCl_2$, 10 mM $MgSO_4$, and 20 mM glucose in deionized water.

TAE buffer was composed of 4.84 g of Tris base, 1.14 ml of glacial acetic acid, 2 ml of 0.5 M EDTA pH 8.0, and deionized water to 1 liter.

TE buffer was composed of 10 mM Tris Base and 1 mM EDTA, pH 8.0.

Example 1

Construction of Reporter Plasmid pSMai226

Reporter plasmid pSMai226 was constructed, as described below, to analyze the strength of Trichoderma reesei promoters using an Aspergillus fumigatus beta-glucosidase as a reporter.

The Aspergillus fumigatus beta-glucosidase coding region and the Trichoderma reesei cellobiohydrolase I (cbh1/cel7a) terminator were amplified from pEJG107 (WO 2005/047499) using primers 069448 and 069449 shown below. The underlined text represents an introduced Sph I site and the italicized text represents a region with homology to the site of insertion in plasmid pMJ09 (WO 2005/056772) for IN-FUSION™ cloning (Clontech Laboratories Inc., Mountain View, Calif., USA).

```
069448:
                                            (SEQ ID NO: 2)
5'-GAATTGTTTAAACGTCGACGCATGCATGAGATTCGGTTGGCTCGA
GGTGGC-3'

069449:
                                            (SEQ ID NO: 3)
5'-CGAAATGGATTGATTGTCTACCGCCAGGTGTCAGT-3'
```

The amplification reaction (50 µl) was composed of 25 ng of pEJG107, 200 µM dNTP each, 0.4 µM primer 069448, 0.4 µM primer 069449, 1× PHUSION® Buffer (New England Biolabs, Ipswich, Mass., USA) and 1 unit of PHUSION® Hot Start High Fidelity DNA polymerase (New England Biolabs, Ipswich, Mass., USA). The reaction was incubated in an EPPENDORF® MASTERCYCLER® (Eppendorf AG, Hamburg, Germany) programmed for 1 cycle at 98° C. for 30 seconds; 30 cycles each at 98° C. for 30 seconds, 60° C. for 30 seconds, and 72° C. for 3 minutes 30 seconds; and 1 cycle at 72° C. for 15 minutes.

The reaction products were separated by 1% agarose gel electrophoresis using TAE buffer where a 3610 bp fragment was excised from the gel and purified using a MINELUTE® Gel Extraction Kit (QIAGEN Inc., Valencia, Calif., USA) according to the manufacturer's instructions.

Plasmid pMJ09 was digested with Acc I where a 5.6 kb fragment comprising the *Aspergillus nidulans* fungal acetamidase gene (amdS) was purified by 1% agarose gel electrophoresis using TAE buffer, excised from the gel, and purified using a MINELUTE® Gel Extraction Kit according to the manufacturer's instructions.

Figure 1:
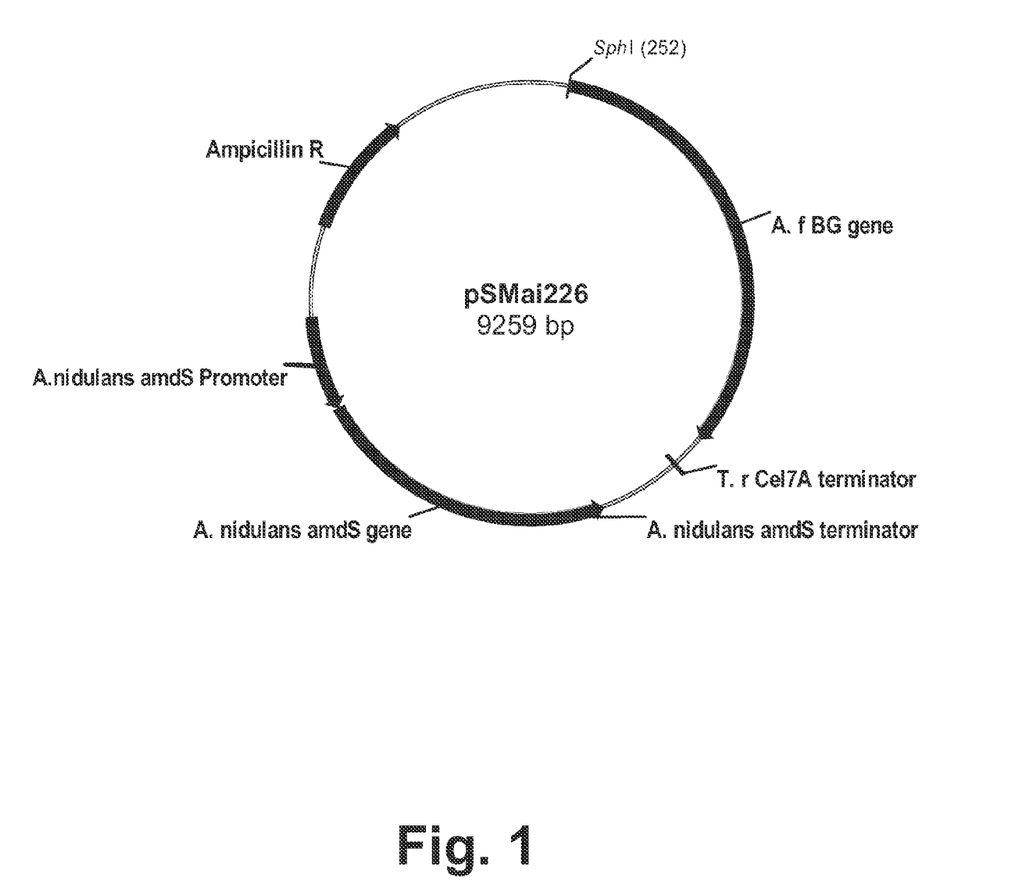
FIG. 1 shows a restriction map of pSMai226.

The 3610 bp PCR fragment was then ligated to the 5.6 kb fragment of Acc I digested pMJ09 using an IN-FUSION™ ADVANTAGE™ PCR Cloning Kit (Clontech Laboratories Inc., Mountain View, Calif., USA) according to the manufacturer's instructions to provide pSMai226 (FIG. 1). The ligation reaction mixture (10 µl) was composed of 1× IN-FUSION™ buffer, 1 µl of IN-FUSION™ enzyme, 100 ng of digested pMJ09 fragment, and 63.5 ng of the purified 3610 bp PCR fragment. The reaction mixture was incubated at 37° C. for 15 minutes, followed by 15 minutes at 50° C. After diluting the reaction mixture with 50 µl of TE buffer (pH 8), 2.5 µl of the reaction was used to transform *E. coli* ONE SHOT® TOP10 competent cells according to the manufacturer's protocol (Invitrogen, Carlsbad, Calif., USA). An *E. coli* transformant containing pSMai226 was detected by restriction digestion with Sph I and Spe I and plasmid DNA was prepared using a BIOROBOT® 9600 (QIAGEN Inc., Valencia, Calif., USA). The *Aspergillus fumigatus* beta-glucosidase gene and the *Trichoderma reesei* cellobiohydrolase I terminator insert in pSMai226 were confirmed by DNA sequencing.

Example 2

*Trichoderma reesei* Strain RutC30 Genomic DNA Extraction

*Trichoderma reesei* strain RutC30 was grown in 50 ml of YEG medium in a baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

Example 3

Construction of Plasmid pSaMe-CatP

Plasmid pSaMe-CatP was constructed, as described below, to comprise the *Trichoderma reesei* catalase promoter, the *Aspergillus fumigatus* beta-glucosidase coding sequence, and the *Trichoderma reesei* cellobiohydrolase I gene terminator.

The 872 bp *Trichoderma reesei* catalase promoter region was amplified from *Trichoderma reesei* RutC30 genomic DNA using primers 069728 and 069729 shown below. The italicized text represents a region with homology to the site of insertion in plasmid pSMai226 for IN-FUSION™ cloning.

```
Primer 069728:
                                            (SEQ ID NO: 4)
5'-AACGTCGACGCATGCTTGTGCACGGCTTTGGGTTAGCAAA-3'

Primer 069729:
                                            (SEQ ID NO: 5)
5'-CCAACCGAATCTCATTTTTGCTGTTCTCGTTGGTT-3'
```

The amplification reaction (50 µl) was composed of Pfx Amplification Buffer (Invitrogen, Carlsbad, Calif., USA), 200 µM dNTP each, 50 ng of *T. reesei* RutC30 genomic DNA, 0.4 µM primer 069728, 0.4 µM primer 069729, 25 mM MgSO$_4$, and 2.5 units of Pfx DNA polymerase (Invitrogen, Carlsbad, Calif., USA). The reactions were incubated in an EPPENDORF® MASTERCYCLER® 5333 programmed for 1 cycle at 95° C. for 2 minutes; 30 cycles each at 95° C. for 15 seconds, 55° C. for 30 seconds, and 68° C. for 1 minute; and one cycle at 68° C. for 7 minutes.

The PCR reaction products were separated by 1% agarose gel electrophoresis using TAE buffer where the 872 bp catalase promoter was excised from the gel and purified using a MINELUTE® Gel Extraction Kit according to the manufacturer's instructions.

Plasmid pSMai226 was digested with Sph I where a 9.2 kb fragment was purified by 1% agarose gel electrophoresis using TAE buffer, excised from the gel, and purified using a MINELUTE® Gel Extraction Kit according to the manufacturer's instructions.

Figure 2:
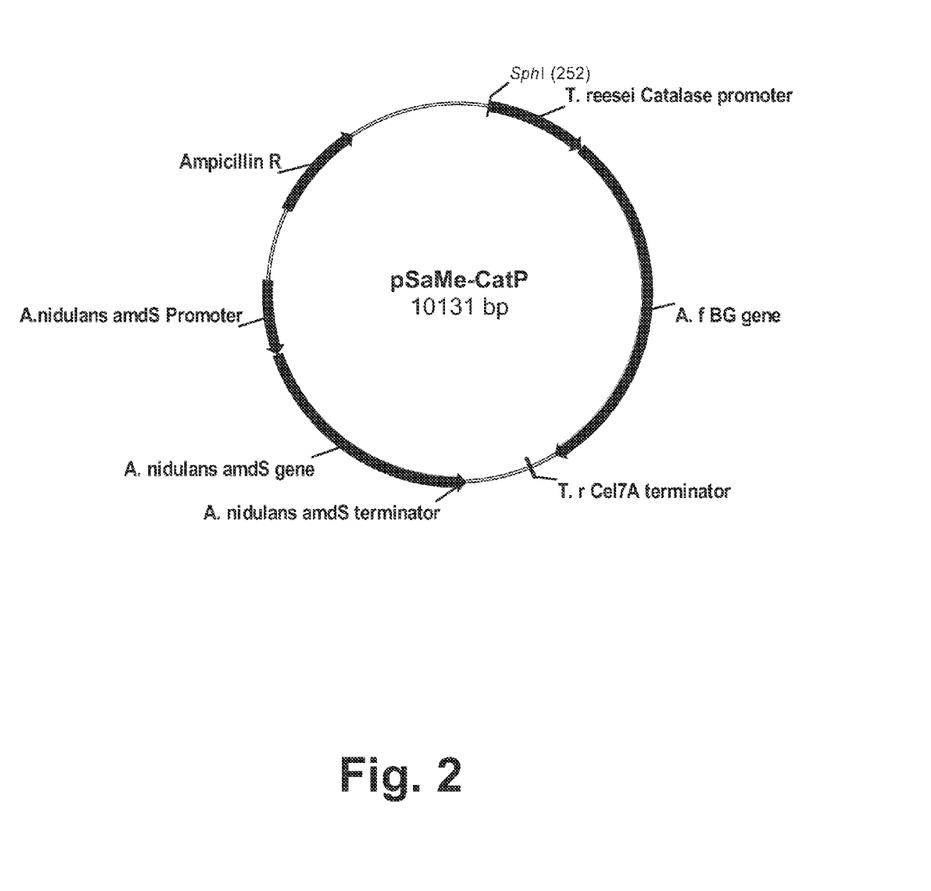
FIG. 2 shows a restriction map of pSaMe-CatP.
Figure 3:
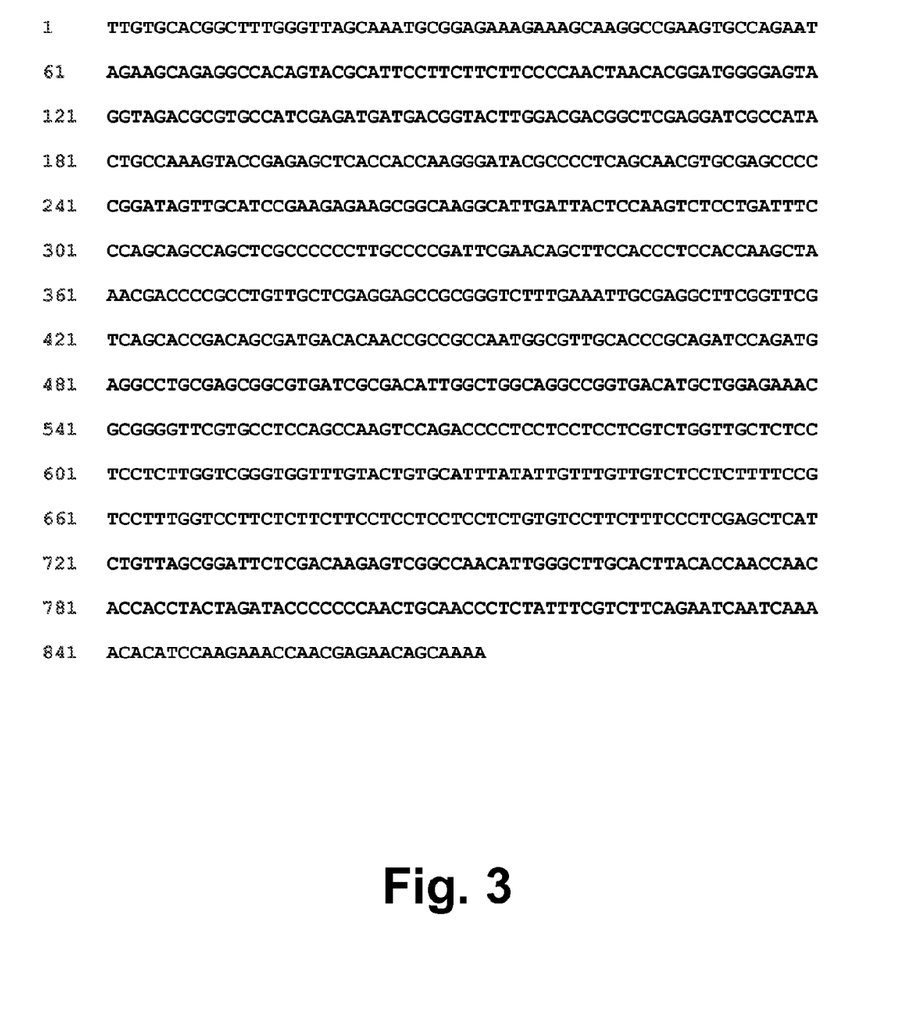
FIG. 3 shows the DNA sequence of a *Trichoderma reesei* catalase promoter (SEQ ID NO: 1).

The 872 bp PCR fragment was than ligated to 9.2 kb fragment of the Sph I digested pSMai226 fragment using an IN-FUSION™ ADVANTAGE™ PCR Cloning Kit according to the manufacturer's instructions to provide pSaMe-CatP (FIG. 2). The ligation reaction mixture (10 µl) was composed of 1× IN-FUSION™ Buffer, 1 µl of IN-FUSION™ enzyme, 200 ng of digested pSMai226, and 36 ng of the purified 872 bp PCR product. The reaction mixture was incubated at 37° C. for 15 minutes, followed by 15 minutes at 50° C. After diluting the reaction mix with 50 µl of TE buffer (pH 8), 2.5 µl of the reaction were used to transform *E. coli* SOLOPACK® Gold competent cells (Agilent Technologies, Palo Alto, Calif., USA) according manufacturer's instructions. An *E. coli* transformant containing pSaMe-CatP was detected by digestion and plasmid DNA was prepared using a BIOROBOT® 9600. The *Trichoderma reesei* catalase promoter insert in pSaMe-CatP was confirmed by DNA sequencing (SEQ ID NO: 1; see FIG. 3).

Example 4

Expression of the *Aspergillus fumigatus* Beta-Glucosidase Utilizing the *Trichoderma reesei* Catalase Promoter Plasmid pSaMe-CatP encoding the mature *Aspergillus fumigatus* beta-glucosidase operably linked to the *Trichoderma reesei* catalase promoter (Example 3) was introduced into *Trichoderma reesei* RutC30-2 by PEG-mediated transformation (Penttila at al., 1987, *Gene* 61: 155-164). The plasmid contained the *Aspergillus nidulans* amdS gene to enable transformants to grow on acetamide as the sole nitrogen source.

*Trichoderma reesei* RutC30-2 was cultivated at 27° C. and 90 rpm in 25 ml of YP medium supplemented with 2% (w/v) glucose and 10 mM uridine for 17 hours. Mycelia was collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg/ml of GLU-CANEX™ (Novozymes A/S, Bagsværd, Denmark) and 0.36 units/ml of chitinase (Sigma Chemical Co., St. Louis, Mo., USA) and incubating for 15-25 minutes at 34° C. with gentle shaking at 90 rpm. The protoplasts were collected by centrifuging for 7 minutes at 400×g and washed twice with cold 1.2 M sorbitol. The protoplasts were counted using a haemacytometer and re-suspended in STC to a final concentration of $1 \times 10^8$ protoplasts per ml. Excess protoplasts were stored in a Cryo 1° C. Freezing Container (Nalgene, Rochester, N.Y., USA) at −80° C.

Approximately 2 μg of pSaMe-CatP digested with Pme I was added to 100 μl of protoplast solution above and mixed gently, followed by addition of 200 μl of PEG buffer, mixing, and incubation at 30° C. for 30 minutes. STC (3 ml) was then added with mixing, and the transformation solution was streaked onto COVE plates using *Aspergillus nidulans* amdS selection. The plates were incubated at 28° C. for 5-7 days. Transformants were sub-cultured onto COVE2 plates and grown at 28° C. Twenty-one transformants were selected and subcultured onto fresh plates containing acetamide and allowed to sporulate for 7 days at 28° C.

The selected *Trichoderma reesei* transformants were cultivated in 125 ml baffled shake flasks containing 25 ml of cellulase-inducing medium at pH 6.0 and incubated at 28° C. and 200 rpm for 5 days. *Trichoderma reesei* RutC30-2 was run as a control. Culture broth samples were removed at day 5 and 1 ml of each culture broth was centrifuged at 13,000×g for 5 minutes and the supernatants transferred to new tubes and stored at 4° C. until assayed for beta-glucosidase activity.

Beta-glucosidase activity in the supernatants above was determined at ambient temperature using 25 μl aliquots of culture supernatants, diluted 1:10 in 50 mM succinate pH 5.0, using 200 μl of 0.5 mg/ml p-nitrophenyl-beta-D-glucopyranoside as substrate in 50 mM succinate pH 5.0. After 15 minutes of incubation the reaction was stopped by adding 100 μl of 1 M Tris-HCl pH 8.0 and the absorbance was read spectrophotometrically at 405 nm. One unit of beta-glucosidase activity corresponded to production of 1 μmole of p-nitrophenyl per minute per liter at pH 5.0 and ambient temperature. *Aspergillus niger* beta-glucosidase (Novozyme 188, Novozymes A/S, Bagsværd, Denmark) was used as an enzyme standard.

The results demonstrated that all assayed transformants showed beta-glucosidase activities higher than the control or parental strain, *Trichoderma reesei* RutC30-2. Transformant SaMe-CatP-19 produced the highest beta-glucosidase activity which was 10-fold higher than the control strain.

SDS-PAGE was performed using CRITERION® Tris-HCl (8-16% resolving) gels (Bio-Rad Laboratories, Inc., Hercules, Calif., USA) with The CRITERION® System (Bio-Rad Laboratories, Inc., Hercules, Calif., USA). Five microliters of each supernatant from day five were suspended in 2× concentration of Laemmli Sample Buffer (Bio-Rad Laboratories, Inc., Hercules, Calif., USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad Laboratories, Inc., Hercules, Calif., USA). The resulting gel was stained with BIO-SAFE® Coomassie Blue G250 protein stain (Bio-Rad Laboratories, Inc., Hercules, Calif., USA).

Twelve of the 21 *Trichoderma reesei* CatP transformants produced a protein of approximately 110 kDa that was not visible in the *Trichoderma reesei* RutC30-2 control. Transformant *Trichoderma reesei* SaMe-CatP-19 produced the highest level of beta-glucosidase.

Example 5

Analysis of Top Transformants in Non-Cellulose Containing Medium

In order to test the strength of the promoter under non-cellulase inducing conditions the top three transformants were cultivated in duplicate in 125 ml baffled shake flasks containing 25 ml of YP and 2% glucose medium and incubated at 28° C. and 200 rpm for 5 days. *Trichoderma reesei* RutC30-2 was run as a control. Culture broth samples were removed at day 5 and one ml sample of each culture broth was centrifuged at 13,000×g for 5 minutes and each supernatant was transferred to a new tube and stored at 4° C. until assayed for beta-glucosidase activity.

Beta-glucosidase activity was determined as described above in Example 4. The results demonstrated that all three transformants exhibited higher beta-glucosidase activity than the control strain *Trichoderma reesei* RutC30-2.

SDS-PAGE was performed as described in Example 4. The results demonstrated that the assay results correlated with the SDS-PAGE results by the presence of an approximately 110 kDa band.

Example 6

Single Spore Isolation of Transformant SaMe-CatP-19

*Trichoderma reesei* transformant SaMe-CatP-19 spores were plated onto a PDA plate and incubated for five days at 34° C. A small area of the confluent spore plate was washed with 0.5 ml of 0.01% TWEEN® 80 to resuspend the spores. A 100 μl aliquot of the spore suspension was diluted to a final volume of 5 ml with 0.01% TWEEN® 80. The spore concentration was determined with a hemocytometer and diluted to a final concentration of 0.1 spores per microliter. A 200 μl aliquot of the spore dilution was plated onto 150 mm COVE2 plates and incubated for 2-3 days at 28° C. Eight emerging colonies were excised from the plate and transferred to PDA plates. After 3 days at 28° C. spores were subcultured on new PDA plates and allowed to grow for an additional 5 days at 28° C. Five of the confluent spore plates were used to inoculate 125 ml baffled shake flasks containing 25 ml of cellulase-inducing medium at pH 6.0 and incubated at 28° C. and 200 rpm for 5 days. *Trichoderma reesei* RutC30-2 was run as a control. Culture broth samples were removed at day 5 and 1 ml of each culture broth was centrifuged at 13,000×g for 5 minutes in a micro-centrifuge and the supernatants transferred to new tubes. Five microliters of each supernatant were mixed with an equal volume of 2× loading buffer (10% beta-mercaptoethanol) and loaded onto a 1.5 mm 8%-16% Tris-Glycine SDS-PAGE gel and stained with BIO-SAFE® Coomassie Blue G250 protein stain. SDS-PAGE profiles of the culture broths showed four of the five transformants were capable of expressing the beta-glucosidase. One transformant, SaMe-CatP-19C, produced the highest yields.

Example 7

Fermentation of Transformant SaMe-CatP-19C

*Trichoderma reesei* SaMe-CatP-19C and control strain *Trichoderma reesei* RutC30-2 were fermented in duplicate in two-liter fermentations and tested for beta-glucosidase activity. Spores of *Trichoderma reesei* SaMe-CatP-19C and *Trichoderma reesei* RutC30-2 grown on PDA plates were inoculated into 500 ml shake flasks containing 100 ml of shake flask medium composed of standard carbon and nitrogen sources. The flasks were placed into an orbital shaker at 28° C. for approximately 48 hours. Fifty ml of the culture was added to a three liter glass jacketed fermentor (Applikon Biotechnology, Inc., Foster City, Calif., USA) containing 1.8 liters of fermentation batch medium composed of standard carbon and nitrogen sources. Fermentation feed medium composed of standard carbon and nitrogen sources was dosed at a rate of 0 to 4 g/L/hr for a period of 185 hours. The fermentation vessel was maintained at a temperature of 28° C. and pH was controlled using an Applikon 1030 control system (Applikon Biotechnology, Inc., Foster City, Calif., USA) to a set-point of 4.5+/−0.1. Air was added to the vessel at a rate of 1 vvm and the broth was agitated by Rushton impeller rotating at 1100 to 1300 rpm. Following fermentation, whole broth was harvested from the vessel and centrifuged at 3000×g to remove the biomass. The supernatant was sterile filtered and stored at 5 to 10° C.

The samples were assayed for beta-glucosidase activity as described above in Example 4. *Trichoderma reesei* SaMe-CatP-19C exhibited higher beta-glucosidase activity than the control strain *Trichoderma reesei* RutC30-2. Total protein levels of both *Trichoderma reesei* SaMe-CatP-19C and the control strain *Trichoderma reesei* RutC30-2 were comparable.

The present invention is further described by the following numbered paragraphs:

[1] A method for producing a polypeptide, comprising; (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence having at least 60% sequence identity to SEQ ID NO: 1, (ii) a promoter comprising a nucleotide sequence that hybridizes under at least medium stringency conditions with SEQ ID NO: 1; or the full-length complement thereof; (iii) a promoter comprising SEQ ID NO; 1; (iv) a promoter comprising a subsequence of (i), (ii), or (iii) that retains promoter activity; and (v) a mutant, hybrid, or tandem promoter of (i), (ii), (iii), or (iv); wherein the polynucleotide encoding the polypeptide is foreign to the promoter; and (b) isolating the polypeptide from the cultivation medium.

[2] The method of paragraph 1, wherein the promoter comprises a nucleotide sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 1.

[3] The method of paragraph 1, wherein the promoter comprises a nucleotide sequence that hybridizes under medium stringency conditions, medium-high stringency conditions, high stringency conditions, or very high stringency conditions with SEQ ID NO: 1 or the full-length complement thereof.

[4] The method of paragraph 1, wherein the promoter comprises or consists of the polynucleotide sequence of SEQ ID NO: 1 or a subsequence thereof that has promoter activity.

[5] The method of paragraph 4, wherein the promoter comprises or consists of the polynucleotide sequence of SEQ ID NO: 1.

[6] The method of paragraph 1, wherein the promoter is a hybrid promoter comp one or more (e.g., several) portions of the polynucleotide sequences of SEQ ID NO: 1.

[7] The method of paragraph 1, wherein the promoter is a tandem promoter comprising one or more (e.g., several) polynucleotide sequences of SEQ ID NO: 1 or a subsequence thereof that retains promoter activity.

[8] The method of paragraph 7, wherein the promoter is a tandem promoter comprising one or more (e.g., several) polynucleotide sequences of SEQ ID NO: 1.

[9] The method of paragraph 7 or 8, wherein the tandem promoter comprises two or more (e.g., several) promoters.

[10] The method of paragraph 9, wherein the two or more (e.g., several) promoters of the tandem promoter simultaneously promote the transcription of the polynucleotide.

[11] The method of paragraph 10, wherein one or more (e.g., several) of the two or more (e.g., several) promoters of the tandem promoter promote the transcription of the polynucleotide encoding the polypeptide at different stages of growth of the fungal host cell.

[12] The method of any of paragraphs 1-11, wherein the fungal host cell contains one or more (e.g., several) copies of the polynucleotide encoding the polypeptide.

[13] The method of any of paragraphs 1-11, wherein the fungal host cell contains one copy of the polynucleotide encoding the polypeptide.

[14] The method of any of paragraphs 1-13, wherein the polypeptide is selected from the group consisting of an antigen, enzyme, growth factor, hormone, immunodilator, neurotransmitter, receptor, reporter protein, structural protein, and transcription factor.

[15] The method of any of paragraphs 1-14, wherein the polypeptide is native or foreign to the fungal host cell.

[16] The method of any of paragraphs 1-15, wherein the polynucleotide is contained in the chromosome of the fungal host cell.

[17] The method of paragraph 1, wherein the polynucleotide is contained on an extrachromosomal element.

[18] The method of any of paragraphs 1-17, wherein the fungal host cell is a filamentous fungal cell.

[19] The method of any of paragraphs 1-17, wherein the fungal host cell is a yeast cell.

[20] An isolated promoter selected from the group consisting of (i) a promoter comprising a nucleotide sequence having at least 60% sequence identity to SEQ ID NO: 1; (ii) a promoter comprising a nucleotide sequence that hybridizes under at least medium stringency conditions with SEQ ID NO: 1 or the full-length complement thereof; (iii) a promoter comprising SEQ ID NO: 1; (iv) a promoter comprising a subsequence of (i), (ii), or (iii) that retains promoter activity; and (v) a mutant, hybrid, or tandem promoter of (l), (ii), (iii), or (iv).

[21] The promoter of paragraph 20, which comprises a nucleotide sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 1.

[22] The promoter of paragraph 20, which comprises a nucleotide sequence that hybridizes under medium stringency conditions, medium-high stringency conditions, high stringency conditions, or very high stringency conditions with SEQ ID NO: 1 or the full-length complement thereof.

[23] The promoter of paragraph 20, which comprises or consists of the polynucleotide sequence of SEQ ID NO: 1 or a subsequence thereof that has promoter activity.

[24] The promoter of paragraph 23, which comprises or consists of the polynucleotide sequence of SEQ ID NO: 1.

[25] The promoter of paragraph 20, which is a hybrid promoter comprising more (e.g., several) portions of the polynucleotide sequences of SEQ ID NO: 1.

[26] The promoter of paragraph 20, which is a tandem promoter comprising one or more (e.g., several) polynucleotide sequences of SEQ ID NO: 1 or a subsequence thereof that retains promoter activity.

[27] The promoter of paragraph 26, which is a tandem promoter comprising one or more (e.g., several) polynucleotide sequences of SEQ ID NO: 1.

[28] The promoter of paragraph 26 or 27, wherein the tandem promoter comprises two or more (e.g., several) promoters.

[29] The promoter of paragraph 28, wherein the two or more (e.g., several) promoters of the tandem promoter simultaneously promote the transcription of a polynucleotide encoding a polypeptide.

[30] The promoter of paragraph 28, wherein one or more (e.g., several) of the two or more (e.g., several) promoters of the tandem promoter promote the transcription of a polynucleotide encoding a polypeptide at different stages of growth of the fungal host cell.

[31] A nucleic acid construct comprising a polynucleotide encoding a polypeptide operably linked to the promoter of any of paragraphs 20-30.

[32] A recombinant expression vector comprising the nucleic acid construct of paragraph 31.

[33] A recombinant host cell comprising the nucleic acid construct of paragraph 31

[34] The recombinant host cell of paragraph 33, which is a filamentous fungal cell.

[35] The recombinant host cell of paragraph 33, which is a yeast cell.

[36] A nucleic acid construct comprising (a) a targeting sequence, (b) the promoter of any of paragraphs 20-30, (c) an exon, and (d) a splice-donor site.

[37] A nucleic acid construct comprising (a) a targeting sequence, (b) a promoter of any of paragraphs 20-30, (c) an exon, (d) a splice-donor site, (e) an intron, and (f) a splice-acceptor site, wherein the targeting sequence directs the integration of elements (a)-(f) such that elements (b)-(f) are operably linked to an endogenous gene

[38] A method for producing a polypeptide comprising (a) cultivating a homologously recombinant cell, having incorporated therein a transcription unit comprising a promoter of any of paragraphs 20-30, an exon, and/or a splice donor site operably linked to a second exon of an endogenous polynucleotide encoding the polypeptide, under conditions conducive for production of the polypeptide, wherein the polynucleotide encoding the polypeptide is foreign to the promoter; and (b) recovering the polypeptide.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide, comprising:
   (a) cultivating a fungal host cell in a medium conducive for the production of the polypeptide, wherein the fungal host cell comprises a polynucleotide encoding the polypeptide operably linked to a promoter selected from the group consisting of (i) a promoter comprising a nucleotide sequence that has at least 95% sequence identity to SEQ ID NO: 1; and (ii) a promoter comprising SEQ ID NO: 1; wherein the polynucleotide encoding the polypeptide is foreign to the promoter; and
   (b) isolating the polypeptide from the cultivation medium.

2. The method of claim 1, wherein the promoter comprises the polynucleotide sequence of SEQ ID NO: 1.

3. The method of claim 1, wherein one or more portions of the promoter sequence of SEQ ID NO: 1 is contained in a hybrid promoter.

4. The method of claim 1, wherein the promoter sequence of SEQ ID NO: 1 is contained in a tandem promoter.

5. The method of claim 1, wherein the polypeptide is foreign to the fungal host cell.

6. The method of claim 1, wherein the fungal host cell is a filamentous fungal cell.

7. The method of claim 1, wherein the fungal host cell is a yeast cell.

8. The method of claim 1, wherein the promoter comprises a nucleotide sequence having at least 96% sequence identity to SEQ ID NO: 1.

9. The method of claim 1, wherein the promoter comprises a nucleotide sequence having at least 97% sequence identity to SEQ ID NO: 1.

10. The method of claim 1, wherein the promoter comprises a nucleotide sequence having at least 98% sequence identity to SEQ ID NO: 1.

11. The method of claim 1, wherein the promoter comprises a nucleotide sequence having at least 99% sequence identity to SEQ ID NO: 1.

* * * * *

SEQUENCE LISTING

```
<160> NUMBER OF SEQ ID NOS: 5

<210> SEQ ID NO 1
<211> LENGTH: 872
<212> TYPE: DNA
<213> ORGANISM: Trichoderma reesei

<400> SEQUENCE: 1
ttgtgcacgg ctttgggtta gcaaatgcgg agaaagaaag caaggccgaa gtgccagaat      60
agaagcagag gccacagtac gcattccttc ttcttcccca actaacacgg atggggagta    120
ggtagacgcg tgccatcgag atgatgacgg tacttggacg acggctcgag gatcgccata    180
ctgccaaagt accgagagct caccaccaag ggatacgccc ctcagcaacg tgcgagcccc    240
cggatagttg catccgaaga gaagcggcaa ggcattgatt actccaagtc tcctgatttc    300
ccagcagcca gctcgccccc cttgcccga ttcgaacagc ttccaccctc caccaagcta    360
aacgaccccg cctgttgctc gaggagccgc gggtctttga aattgcgagg cttcggttcg    420
```

```
tcagcaccga cagcgatgac acaaccgccg ccaatggcgt tgcacccgca gatccagatg      480
aggcctgcga gcggcgtgat cgcgacattg gctggcaggc cggtgacatg ctggagaaac      540
gcggggttcg tgcctccagc caagtccaga cccctcctcc tcctcgtctg gttgctctcc      600
tcctcttggt cgggtggttt gtactgtgca tttatattgt ttgttgtctc ctcttttccg      660
tcctttggtc cttctcttct tcctcctcct cctctgtgtc cttctttccc tcgagctcat      720
ctgttagcgg attctcgaca agagtcggcc aacattgggc ttgcacttac accaaccaac      780
accacctact agataccccc ccaactgcaa ccctctattt cgtcttcaga atcaatcaaa      840
acacatccaa gaaaccaacg agaacagcaa aa                                    872

<210> SEQ ID NO 2
<211> LENGTH: 51
<212> TYPE: DNA
<213> ORGANISM: Aspergillus fumigatus

<400> SEQUENCE: 2
gaattgttta aacgtcgacg catgcatgag attcggttgg ctcgaggtgg c              51

<210> SEQ ID NO 3
<211> LENGTH: 35
<212> TYPE: DNA
<213> ORGANISM: Aspergillus fumigatus

<400> SEQUENCE: 3
cgaaatggat tgattgtcta ccgccaggtg tcagt                                35

<210> SEQ ID NO 4
<211> LENGTH: 40
<212> TYPE: DNA
<213> ORGANISM: Trichoderma reesei

<400> SEQUENCE: 4
aacgtcgacg catgcttgtg cacggctttg ggttagcaaa                           40

<210> SEQ ID NO 5
<211> LENGTH: 35
<212> TYPE: DNA
<213> ORGANISM: Trichoderma reesei

<400> SEQUENCE: 5
ccaaccgaat ctcattttg ctgttctcgt tggtt                                 35
```